United States Patent [19]
von Nettelhorst

[11] 4,261,370
[45] Apr. 14, 1981

[54] APPARATUS FOR DETECTING ARRHYTHMIAS

[76] Inventor: Herwig von Nettelhorst, Pössnecker Strasse 30, D-1000 Berlin, Fed. Rep. of Germany

[21] Appl. No.: 35,087

[22] Filed: May 1, 1979

[30] Foreign Application Priority Data

May 3, 1978 [DE] Fed. Rep. of Germany ....... 2819757

[51] Int. Cl.$^3$ .............................................. A61B 5/04
[52] U.S. Cl. .................................................. 128/702
[58] Field of Search ............................... 128/689-690, 128/701-706

[56] References Cited

U.S. PATENT DOCUMENTS

| | | | |
|---|---|---|---|
| 3,593,705 | 7/1971 | Thomas et al. | 128/703 |
| 3,755,783 | 8/1973 | Astarjian et al. | 128/702 |
| 3,773,038 | 11/1973 | Smith et al. | 128/706 |
| 3,881,467 | 5/1975 | Stanly et al. | 128/702 |
| 3,998,214 | 12/1976 | Garrison | 128/702 |

FOREIGN PATENT DOCUMENTS

| | | | |
|---|---|---|---|
| 2152093 | 4/1973 | Fed. Rep. of Germany | 128/703 |
| 2736541 | 2/1979 | Fed. Rep. of Germany | 128/706 |

OTHER PUBLICATIONS

Kyle, D. G. et al., "A Recognition System for the Detection of Cardiac Arrythmias", Conf: Proc. of the Conf. on Applic. of Electronics in Medicine, Southhampton, Eng. 6-8 Apr. 1976, pp. 223-228.

Mattis, J. A. et al., "A New PLL with High Stability and Accuracy (SE/NE 565)", Signetics Corp., Sunnyvale Calif.

von Nettelhorst H., "Heart Frequency Tracking Histogram Device", Bio-medical Art, vol. 22, No. 3, 1977, pp. 60-62.

Primary Examiner—Robert W. Michell
Assistant Examiner—Francis J. Jaworski
Attorney, Agent, or Firm—Spencer & Kaye

[57] ABSTRACT

Apparatus for detecting arrhythmias in an electrocardiogram signal by evaluating the time interval between signals which are consecutive in time and which are characteristic for a heartbeat, including a circuit for producing pulses at a frequency which follows the actual heart frequency and which is a multiple thereof and with a time constant, and a gating circuit which emits a signal indicating an arrhythmia if before the n$^{th}$ pulse produced after the last heartbeat a further such characteristic signal appears, where n is smaller than the multiple.

12 Claims, 8 Drawing Figures

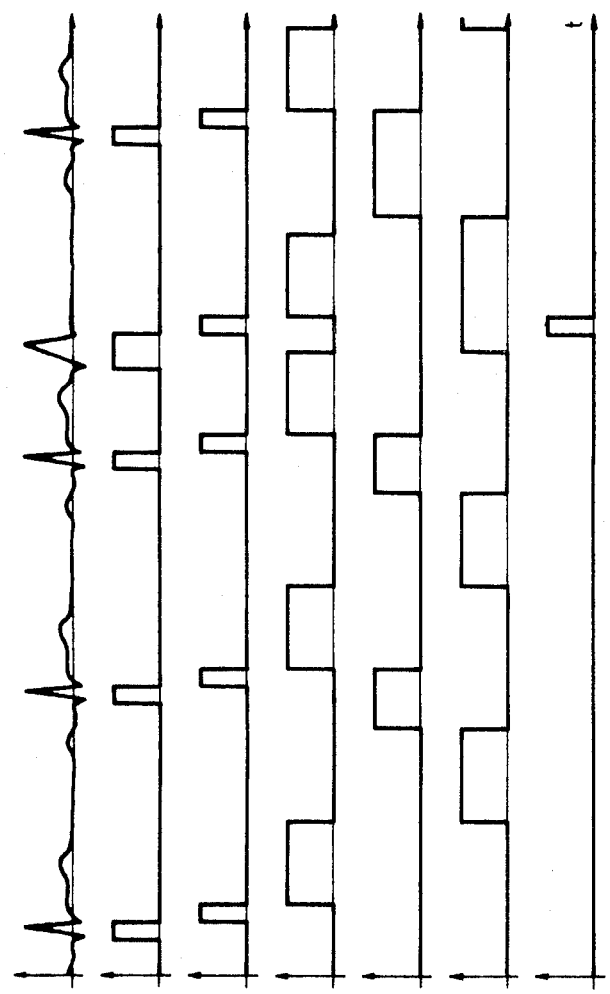

APPARATUS FOR DETECTING ARRHYTHMIAS

BACKGROUND OF THE INVENTION

The present invention relates to an apparatus for detecting arrhythmias in electrocardiogram signals by evaluating the time interval between signals which succeed one another in time and which are characteristic for a heartbeat.

It is known to obtain information about the activity of a patient's heart by a real time evaluation of the appearance of signal components in the EKG. Since cardiac activity, however, in dependence on stress, medication etc. is subject to time-dependent changes, it is necessary, in order to obtain a precise diagnosis, to monitor the cardiac behavior over a long period of time, in some cases several days.

In order for the physician or his assistant not to be required to continuously visually follow the curves of the electrocardiogram, automatically operating histogram stores, or memories, have been developed which determine the time elapsed between successive heartbeats and store a representation of that time in counters in separate classified arrangements so that at the end of the monitoring period an overview of the statistical distribution of the heartbeat rates is available.

However, with this method it is not possible to obtain information about the dynamics of the heartbeat behavior, i.e. to indicate how the heart rate has changed in the course of time. For example, in the case of a particular kind of change, it can not be determined whether, over a relatively long period of time, a patient had bradycardia as well as tachycardia or experienced double beat phenomena, i.e. an alternation between two heartbeat rates, from one to the other.

Attempts have been made in this connection to obtain information about changes in cardiac activity from one heartbeat to the next by recording so-called difference histograms in that the times between two successive heartbeats are compared. If the time deviation exceeds a given difference value, a signal indicating an arrhythmia is emitted. In this case the differences in the times between two successive heartbeats are also classified as to time and are stored in different counters so that at the end of the monitoring period the statistical distribution of the differences in times between two successive heartbeats is available.

This solution has the drawback that the determined absolute time differences permit no accurate conclusion regarding the patient's cardiac behavior. The determined and recorded time differences exhibit a much greater value for coinciding determinations at slow heartbeat rates than at fast heartbeat rates so that erroneous interpretations cannot be excluded. During recording over a long period of time with the aid of a histogram store, subsequent association of the time differences recorded with the aid of counters with the different heartbeat rates that have occurred is not possible.

U.S. Pat. No. 3,755,783 discloses an analyzer for biomedical signals in which irregularities in the cardiac rhythm are determined by classifying the signals characteristic for heartbeats with respect to the time elapsed since the respective previous heartbeat. Since in this classification all time periods which serve as a standard are fixed, these must always be selected to be lower than the shortest time period between two successive regular heartbeats to be expected. However, at a low heart rate, a heartbeat following at a time interval which for a high heart rate would still be regular already indicates an arrhythmia. Therefore, this prior art analyzer cannot detect all irregularities in a heart rhythm.

SUMMARY OF THE INVENTION

It is an object of the present invention to obtain correct information about the dynamic behavior of the heart with the aid of the determined data during the monitoring period.

These and other objects are achieved, according to the invention, in apparatus for detecting arrhythmias in an electrocardiogram signal composed of time consecutive signal components which are characteristic of a heartbeat, by evaluating the time interval between immediately succeeding components, by the provision of sensing circuit means connected to respond to such signal for producing pulses at a frequency which is a multiple of, and follows, with a selected time constant, the actual heartbeat rate, and at least one gating circuit connected to produce a signal indicating an arrhythmia it before the $r^{th}$ pulse produced by the sensing circuit means after the last heartbeat characteristic signal component a further such signal component appears, where n is less than the frequency multiple.

The present invention is based on the discovery that a reliable diagnosis based on the time changes of cardiac behavior is possible only if the cardiac activities are evaluated under consideration of the actual heartbeat frequency in such a way that the applicable time differences or comparison times are controlled to be proportional to the heart frequency.

Preferred embodiments of the apparatus according to the present invention are constructed according to a simple design and are produced from commercially available integrated components in a portable arrangement which can be worn on the body of the patient to be examined. Thus evaluation of cardiac activity is not limited to the situation of physical movement during an examination in the physician's office but can be made under normal conditions encountered in the daily life of the patient.

A further advantage of the present invention is that, in most cases, it permits reliable information about the cardiac activity to be obtained even after examination periods of only a few minutes.

Preferred embodiments of the invention utilize a PLL system, which permits a particularly simple and reliable design for the apparatus. Here the oscillator frequency of the PLL system is selected to be higher than the cardiac frequency and serves as the clock signal to determine the time limit values which constitute the standard for the evaluation of the cardiac activity.

The apparatus according to the present invention for detecting arrhythmias can be combined with an instrument for detecting the heart frequency, particularly for classified recording in the form of a histogram, the information obtained regarding the heart frequencies that have occurred and the arrhythmias connected therewith advantageously supplementing one another. It is particularly advantageous, in this connection, if the instrument or unit for determining and recording the heart frequency histogram has the form disclosed in German Patent Application No. P 27 36 541.9. In this case, a single PLL system can be used to measure and record heart frequency, as well as to detect arrhythmias, so that the design can be particularly economical and energy saving, which is of particular importance for a portable arrangement. Identical memories can be used for the classified recording of heartbeat rates and arrhythmias. The oscillator frequency of the PLL system is advisably selected so that is equals 60 times the heartbeat rate.

This results in the further advantage that the apparatus for detecting arrhythmias can simply be an accessory for the device to determine the histogram, a device that can be attached, for example, by means of a plug-in connection.

The recording of the detected arrhythmias, in the basic design providing a simple structure, is effected with a single counter having a direct read-out. For certain applications, however, variations are possible which by appropriate logic linkages of the signals representative of the events and suitable association of counters also permit classification of the arrhythmias in dependence on their occurrence in time in the EKG and on the current, instantaneous, heart frequency.

By appropriately determining the gating periods employed, it is then also possible to detect very prematurely occurring extrasystoles which fall under the vulnerable phase of the heart.

According to another preferred embodiment, an additional waveform criterion of the electrocardiogram signals is used for the detection and recording of arrhythmias in order to differentiate between supraventricular and ventricular extrasystoles. The criterion is here a frequency dependent selection of the energy maximum of the occurring heart signals.

BRIEF DESCRIPTION OF THE DRAWING

FIGS. 2a through 2g are diagrams of the amplitude waveforms, with respect to time, of the signals present at certain points in the circuit of FIG. 1.

DESCRIPTION OF THE PREFERRED EMBDOIMENTS

Figure 1:
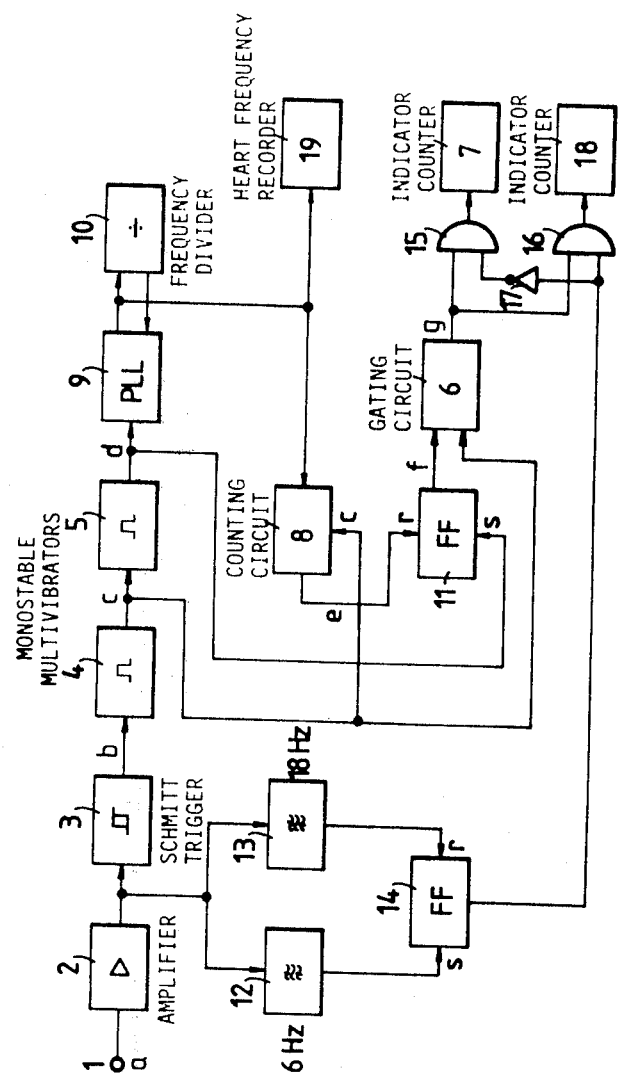
FIG. 1 is a block circuit diagram of a preferred embodiment of apparatus according to the invention.

In the block circuit diagram of the apparatus according to the invention shown in FIG. 1, a cardiac signal derived via conventional EKG electrodes attached to the body of a patient is fed via an input 1 to an amplifier 2 by means of which the level of the cardiac signal is raised for subsequent signal processing. The output signal from amplifier 2 is conducted to the input of a Schmitt trigger 3 at whose output there appears a pulse only in response to each heart signal portion whose amplitude exceeds a given amplitude level (QRS complexes).

Further signal processing is effected via a monostable multivibrator 4 which emits a pulse of a certain duration whenever there is a cardiac signal which exceeds the given level, i.e. in response to each output pulse from trigger circuit 7. Each pulse from multivibrator 4 travels, on the one hand, to a second monostable multivibrator 5 and, on the other hand, to the signal input of a gating circuit 6 where it can be recorded, if additional conditions are met which will be explained below, in an indicator counter 7 as an event, i.e. the occurrence of an arrhythmia.

The monostable multivibrator 4 serves as a pulse shaper, the time duration of its output pulse being selected so that portions of that QRS complex which have already actuated the monostable multivibrator 4 will not produce new pulses which could simulate the occurrence of an arrhythmia.

Signal waveforms appearing on lines a, b, c, d, e, f and g in the circuit of FIG. 1 are shown in correspondingly numbered FIGS. 2a–g.

FIG. 2a shows a simplified waveform of a typical input signal at terminal 1, while FIG. 2b shows the waveform of the corresponding signal at the output of the Schmitt trigger 3 and FIG. 2c shows the waveform of the corresponding signal at the output of the monostable multivibrator 4. As FIGS. 2b and 2c indicate, each pulse from multivibrator 4 is triggered by the trailing edge of a pulse from trigger 3.

A PLL system 9 connected to the output of the second monostable multivibrator 5 produces an oscillation at a frequency which follows a selected multiple of the current, momentary, heart frequency with a time constant.

Design and operation of such a PLL system are described in the publication authored by J. A. Mattis and H. R. Camenzind, entitled "A New Phase Locked Loop with High Stability and Accuracy (SE/NE 565)", particularly FIG. 16, published by the Signetics Corp., of Sunnyvale, California. The time constant of the PLL-system 9 is defined by a low pass filter, which is interposed between the output of the phase-comparator and the output of the VCO. This filter may be active or passive with a response according to the following general type of transfer functions:

$$F(s) = \frac{1 + sT_2}{sT_1} \text{ (active)}$$

$$F(s) = \frac{1 + sT_2}{1 + s(T_1 + T_2)} \text{ (passive)}.$$

The time constants must be selected such that the resonance frequency of the complete PLL-system is lower than the lowest heart rate to be expected.

The voltage dependent oscillator usually included in a PLL system 9, not shown separately in FIG. 1 hereof, is controlled by the output signal from a phase comparison circuit also included in the PLL system 9, which performs a comparison between the phase position of the leading edge of each output pulse from monostable multivibrator 5 and that of a signal from a frequency divider circuit 10. Divider 10 is connected to system 9 to divide the frequency of the oscillator included in the PLL system by a multiple so that the pulses emitted by the divider circuit 10 are essentially at the heart frequency. In the illustrated embodiment the PLL system is synchronized only by the leading edge of the pulses emitted by the multivibrator 5.

A flip-flop 11 connected to the gating input of the gating circuit 6, for controlling that circuit, is set each time through a setting input s by the trailing edge of the pulses emitted by the monostable multivibrator 5. The flip-flop 11 influences the gating circuit 6 in such a manner that the pulses from monostable multivibrator 4 can reach output of circuit 6 only if flip-flop 11 has been set, i.e. if its output is at the electrical high (H), or Logic 1, level.

The flip-flop 11 is reset via its reset input r whenever a counting circuit 8 has reached a given count state n which is less than, and preferably equal to between 0.6 and 0.8 times the heart frequency multiple of the oscillation frequency of the PLL system 9. The counting circuit 8 may here be formed, for example, by a resettable frequency divider circuit which effects frequency reduction of pulses emanating from the oscillator output of the PLL system 9 by a frequency division ratio which is equal to the multiple of PLL system frequency to heartbeat frequency if n is chosen to be equal one half of that multiple so that, after half of the pulses required for a complete heartbeat period in the output signal from system 9 have appeared at the input of circuit 8, the counting circuit output will change its logic state.

The monostable multivibrator 5 serves to suppress the occurrence of T waves appearing in the electrocardiogram signal according to the QRS complex so that such T waves will not lead to the recording of an arrhythmia. Due to the fact that setting of the flip-flop 11, and thus opening of the gating circuit 6, takes place only in response to the trailing edge of the pulse emitted by the monostable multivibrator 5, signals possibly produced by T waves cannot actuate undesirable advancement of the indicator counter 7.

The mode of operation of the apparatus according to the invention for the detection of arrhythmias will now be explained in detail with reference to the other pulse diagrams shown in FIGS. 2d through g.

The counting circuit 8 defines, between the time at which it is set to a starting state by a signal applied to its "clear" input c and the time a given count state is reached timed by the divider circuit 10, a time period in the coarse of which flip-flop 11 is set and pulse-shaped components of the heart signal attributable to arrhythmias can pass to the indicator counter 7 to advance its count state. The output from counting circuit 8 is shown in FIG. 2e, where each pulse depicts the existence of the given count state. This time period until the counting circuit 8 reaches such given state then depends on the frequency at which the oscillator of the PLL system 9 oscillates. Since the PLL system is synchronized with the momentary heart frequency, or relatively quickly adapts itself thereto if there is an occurrence of extrasystoles, the period for detecting pulses indicating arrhythmias in the heart signal is always adapted to the momentary heart frequency.

If the oscillator in the PLL system 9 oscillates, for example, at ten times the heart frequency, the dividing ratio in the divider circuit 10 is likewise 10, and the counting circuit 8 emits a signal after seven pulses at the PLL oscillation frequency to reset the flip-flop 11, 70% of the time between two successive QRS pulses at the momentary heart frequency is utilized to detect arrhythmias, i.e. all other heart signals which actuate a pulse at the output of the monostable multivibrator 4 are evaluated as regular cardiac behavior. These values can of course be modified corresponding to the requirements of the diagnosing problem involved.

If a plurality of circuit groups, each including the gating circuit 6, the indicator counter 7, the counting circuit 8 and the flip-flop 11 is provided, and the counting circuits of the several groups emit their respective signal at different counter states, i.e. create intervals of different duration, it is possible to classify as to time the events connected with the recorded arrhythmias in the heart signal curve in the sense of a histogram. In this case, logic circuitry can be provided to enable another indicator counter via a respective gating circuit, whenever one of the counting circuits has reached its given counting state, to record events so that every signal indicating an arrhythmia will be recorded in only one of the counters.

The particularly simple design of the illustrated embodiment is a result, in particular, of the fact that the counting circuit 8 is actuated by pulses which originate from the PLL system 9, i.e. pulses which are adapted in their frequency to the actual cardiac behavior so that no additional timing means are required and there always exists synchronism with the present heartbeat frequency.

By appropriately dimensioning the time constant of the PLL system it is possible to set the apparatus according to the invention so that normal, slow changes in heart frequency will not lead to an indication while deviations are recognized and recorded at once. This value is selected so that the frequency of the circuit for generating pulses, i.e. the PLL system, adapts itself to the multiple of the actual, or current, heart frequency within the time of two to three heartbeats to the extent that subsequent heartbeats with an essentially constant frequency will not actuate a signal indicating arrhythmia. The setting of the time constant is effected by appropriately dimensioning, in a known manner, an RC member at the control input of the voltage controlled oscillator provided in PLL system 9.

In the above description of the pulse sequences according to FIGS. 2a through 2d it has been assumed that the entire time period in which the output of counting circuit 8 has the electrical low, or Logic 0, state is available for recording arrhythmias. This time period, however, is shortened by the duration of the output pulses, shown in FIG. 2d, of the monostable multivibrator 5 in order to suppress the T waves, as mentioned above. The flip-flop 11 which sets the gate enabling periods of the gating circuit 6 is set only by the trailing edge of the outut pulse of the monostable multivibrator 5. The output state of flip-flop 11 is shown in FIG. 2f, where each gate enabling period is represented by a positive pulse. An inverter (not shown) connected to the output of flip-flop 11 makes it possible to also separately detect and record the pulses occurring in the vulnerable phase of the heart, up to the T wave, which may be important in some diagnostic cases.

In FIG. 2d, the output pulses of the monostable multivibrator 5 are initially shown for regular, or normal, heartbeat behavior. The counting circuit 8 is reset by the trailing edge of each output pulse from the monostable multivibrator 4 and emits an output pulse when the above-mentioned counting state "7" has been reached. FIG. 2f shows how the output of flip-flop 11 takes on the Logic 1 state during the periods between the trailing edge of an output pulse from the monostable multivibrator 5 and the leading edge of the next succeeding output pulse from counting circuit 8.

Upon the occurrence of an extrasystole, as shown for example in FIG. 2a after the third QRS complex, the Schmitt trigger 3 and then also the monostable multivibrator 4 emit an output pulse whereupon the counting circuit 8 is reset again before having reached the given count state. The flip-flop 11, however, remains set, since no reset signal was supplied by circuit 8, so that the then occurring output pulse from the monostable multivibrator 4 reaches the indicator counter 7 via gating circuit 6 and is recorded there. The pulse appearing at the output of gating circuit 6 is shown in FIG. 2g.

The trailing edge of the corresponding output pulse from the monostable multivibrator 5 delayed relative to its leading edge, remains without effect at flip-flop 11 because it is already set. Due to the fact that the leading edge of the same pulse has already reached the PLL system 9 as a reference signal, the frequency of the oscillator of that system is increased because the system tends to adapt itself to this accelerated heart rate. The counting circuit 8 therefore reaches the given count state faster than before, at which time the flip-flop 11 is reset. The output pulse from the monostable multivibrator 4 actuated by the next QRS complex can thus not pass through the gating circuit 6 and is consequently not registered by the indicator counter 7.

If the PLL system 9 follows the actual heart frequency with a time constant selected so that synchronism is obtained within two or three heartbreaks even for large jumps in frequency, it is assured, on the one hand, that normal changes in the heart frequency are not evaluated as arrhythmias but, on the other hand, that double beat phenomena are reliably detected.

With other circuit components also shown in FIG. 1, it is possible to differentiate with respect to shape between superventricular and ventricular extrasystoles and to record them separately. Since the energy maximum of ventricular extrasystoles lies in a lower frequency range at about 6 Hz and, that of superventricular systoles lies in a higher frequency range of about 18 Hz, a filter circuit, composed of a bandpass filter 12 having a pass band of about 6 Hz and a bandpass filter 13 having a pass band of about 18 Hz, connected to the amplifier 2 will be able to determine in which frequency range a detected signal component belongs. With the prerequisite that these filter circuits contain the appropriate pulse shaping circuits, the output signal of bandpass filter 12 actuates the "set" input s of a flip-flop 14 and the output signal of bandpass filter 13 actuates the "reset" input r of this flip-flop 14 which, with the aid of AND gates 15 and 16 as well as an inverter 17 associates the last detected signal either with the indicator counter 7 or a further indicator counter 18 depending on its frequency range. In the illustrated embodiment, ventricular extrasystoles are recorded in indicator counter 18 and superventricular extrasystoles are recorded in indicator counter 7.

Particularly informative for the treating physician is the combined evaluation of the results furnished by the apparatus according to the invention in conjunction with a simultaneously recorded heart frequency histogram. For this purpose, the apparatus is connected directly with a heart frequency recorder 19 of a histogram store, only one set of circuit components for recording and amplifying or shaping the signals being required. Recorder 19 can be constituted by a known device. Since the heart frequency has been increased by a multiple in system 9, a conventional digital frequency meter with relatively short integration period and a readout adjusted to the frequency multiplication can be used for recorder 19. A suitably modified version of recorder 19 could alternatively be connected to the output of divider 10.

For economy reasons, the histogram store may be designed so that the circuit for detecting arrhythmias can be added as required either permanently or temporarily, for example by means of plug-in connections. The possibilities for making housing or electrical connections need not be explained in detail here since they are known to those skilled in the art. Class memories available in the histogram store can also be used for recording the contents of indicator counter 7 or 18, respectively.

If the apparatus according to the invention is used together with a histogram store operating according to the disclosure of German Patent Application No. P 27 36 541.9, the PLL system, including divider circuit 10, provided there is used as well, and the oscillator frequency in the PLL system is selected under consideration of the requirements of both parts of the combined apparatus. The PLL system then operates with a frequency which is equal to 60 times the heart frequency. With this setting, there exists the possibility of adjusting the recording period of the counting circuit 8, i.e. the periods during which arrhythmias can be detected, in sufficiently small steps. If, however, the counting circuit 8 is to be kept as simple as possible, by giving it a low count capacity, it is also possible to tap a suitable lower frequency counter input signal from a frequency divider circuit including a divider chain incorporated into the PLL system.

German Application No. P 27 36 541.9 was laid open for public inspection on February 22nd, 1979.

It will be understood that the above description of the present invention is susceptible to various modifications, changes and adaptations, and the same are intended to be comprehended within the meaning and range of equivalents of the appended claims.

What is claimed is:

1. In apparatus for detecting arrhythmias in an electrocardiogram signal composed of time consecutive signal components which are each characteristic of a heartbeat, by evaluating the time interval between immediately succeeding components characteristic of successive heartbeats, the improvement comprising:

sensing circuit means connected to respond to such signal for producing pulses at a frequency whose value is a multiple of, and follows, with a selected time constant, the actual heartbeat rate;

a counter connected to said sensing circuit for counting the pulses produced thereby in order to produce a count output upon arrival of the $n^{th}$ pulse after each heartbeat characteristic signal component, where n is less than said multiple; and at least one gating circuit connected to said sensing circuit means and to said counter to produce a signal indicating an arrhythmia if a heartbeat characteristic signal component appears at a time after the last-occurring such signal component and before production of the count output associated with such last-occurring signal component.

2. Apparatus as defined in claim 1 wherein the time constant with which the frequency of the pulses produced by said sensing circuit means follows the actual heartbeat rate is dimensioned so that the frequency of the pulses adapts to the actual heart frequency within two or three heartbeats so that the next following heartbeats having a substantially constant frequency will not actuate a signal indicating an arrhythmia.

3. Apparatus as defined in claim 1 or 2 wherein n is between 0.6 and 0.8 times the multiple.

4. Apparatus as defined in claim 1 wherein said sensing circuit means comprise a PLL system including a frequency divider for reducing the frequency of the pulses produced by said sensing circuit means by said multiple, and a phase comparison circuit connected to receive the output signal from said frequency divider and pulses corresponding to said signal components at the actual heartbeat rate as input signals.

5. Apparatus as defined in claim 1 further comprising at least one counter connected to said gating circuit to count each occurrence of such a signal indicating an arrhythmia.

6. Apparatus as defined in claim 1 further comprising additional circuit means connected for deriving an additional signal from the electrocardiogram signal, and means connected for logically linking the signal indicating an arrhythmia with the additional signal.

7. Apparatus as defined in claim 6 wherein each component of the signal is constituted by a QRS complex and said additional circuit means emit the additional signal, following each signal component, for a period still covering the subsequent T wave.

8. Apparatus as defined in claim 7 wherein said sensing circuit means comprise a Schmitt trigger and said means for logically linking act to suppress the electrocardiogram signal for the duration of each additional signal and thus during each period still covering the T wave following each QRS complex.

9. Apparatus as defined in claim 7 wherein said sensing circuit means comprise a Schmitt trigger and said means for logically linking include a separate output connected to receive such signal component for the duration of each additional signal.

10. Apparatus as defined in claim 6 wherein said additional circuit means comprise frequency filters connected to receive the electrocardiogram signal and producing output signals which actuate the additional signal in dependence on frequency components contained in the electrocardiogram signal, and said means for logically linking respond to said additional signal to actuate a signal indicating a ventricular extrasystole if a frequency maximum occurs in the electrocardiogram signal at about 6 Hz and to actuate a signal indicating a superventricular extrasystole if a frequency maximum occurs at about 18 Hz.

11. Apparatus as defined in claim 1 further comprising monitoring means connected to receive the pulses at a frequency which is a multiple of the actual heartbeat rate and to provide an indication of the current heartbeat rate.

12. Apparatus as defined in claim 11 wherein the multiple equals 60 and the frequency of the pulses per second is indicated by said monitoring means as a heart frequency per minute.

* * * * *